United States Patent [19]

Lucero et al.

[11] Patent Number: 5,010,776

[45] Date of Patent: Apr. 30, 1991

[54] ENVIRONMENTAL CONTAMINATION DETECTION AND ANALYZING SYSTEM AND METHOD

[75] Inventors: Daniel P. Lucero, Triangle, Va.; Susan K. Hendrickson, Germantown, Md.

[73] Assignee: IIT Research Institute, Chicago, Ill.

[21] Appl. No.: 347,424

[22] Filed: May 4, 1989

[51] Int. Cl.⁵ .............................................. G01N 1/22
[52] U.S. Cl. ................................................ 73/863.23
[58] Field of Search ........... 73/863.23, 863.24, 863.25, 73/864.73, 864.74

[56] References Cited

U.S. PATENT DOCUMENTS

| | | |
|---|---|---|
| 2,928,247 | 3/1960 | Hubbell . |
| 3,902,068 | 8/1975 | Wood ................................ 73/49.3 X |
| 3,995,472 | 12/1976 | Murray ................................... 73/40 |
| 4,110,947 | 9/1978 | Murray et al. ..................... 405/54 X |
| 4,112,739 | 9/1978 | Lyssy ...................................... 73/38 |
| 4,352,601 | 10/1982 | Valiga et al. ....................... 405/54 X |
| 4,439,062 | 3/1984 | Kingsbury ......................... 405/54 X |
| 4,464,081 | 8/1984 | Hillier et al. ....................... 405/54 X |
| 4,568,925 | 2/1986 | Butts ................................. 73/49.2 X |
| 4,618,855 | 10/1986 | Harding et al. ....................... 340/605 |
| 4,709,577 | 12/1987 | Thompson ............................ 73/40.7 |
| 4,759,227 | 7/1988 | Timmons ........................... 73/863.23 |
| 4,821,565 | 4/1989 | Kampe ............................. 73/863.23 |
| 4,857,473 | 8/1989 | Magerita et al. ............. 73/863.23 X |

FOREIGN PATENT DOCUMENTS 1804441 10/1968 Fed. Rep. of Germany ....... 73/49.2

OTHER PUBLICATIONS

U.S. Army Corp. of Engineers Mar., 1988 Special Report "Preliminary Development of a Fiber Optic Sensor for TNT", Yukezhang et al., pp. i–14 iii and 1–16.
"Formulation and Evaluation of a Hazardous Waste Probe Suitable for Field Applications", Prepared by Dr. Harry Hemond, Prepared for: U.S. Army Construction Engr. Res. Lab., Feb. 1, 1986, pp. 1–80.
EPA Project Summary "Underground Tank Leak Detection Methods: A State-of-the-Art Review", Jul. 1986, EPX/600/S2-86/001; Shahzad Niaki et al., 4 pages.

Primary Examiner—Tom Noland
Attorney, Agent, or Firm—Fitch, Even, Tabin & Flannery

[57] ABSTRACT

A method and system for detecting environmental contamination, such as subsurface contamination, include a test probe located in a medium. The probe is adapted to collect a fluid sample from the medium for determining the presence of a contaminant having a vapor pressure. Pneumatic communication lines extend from a test point and connect to the probe. A detector/analyzer is connected to the distal end of the communication lines of the probe. While connected, a fluid sample is taken into the probe and transported in the pneumatic communication lines by a carrier gas to the detector/analyzer for analysis of the contaminant. The general principle is applicable for contaminant detection and/or analysis in soil masses, liquid masses and gases.

6 Claims, 5 Drawing Sheets

ENVIRONMENTAL CONTAMINATION DETECTION AND ANALYZING SYSTEM AND METHOD

This invention relates to a system and method for the in situ detection and analysis of contaminants in subsoil gases and liquids, in liquid masses and in gases.

BACKGROUND OF THE INVENTION

The storage of liquids and gases, the treatment of waste, particularly hazardous waste, the disposal of waste material and monitoring thereof have been the subject of considerable public attention. Although in some matters of public concern, a passive attitude is the norm, the direct relationship between landfill disposal of waste, hazardous waste, the storage of liquids and gas on the one hand and groundwater pollution on the other is particularly critical because of a potential direct link between toxic substances and a person's water faucet. Thus, the public is more active, and even sometimes volatile, in expressing concern in these matters. Groundwater pollution in most instances is not detectable to the human eye and is identified only when the pollution reaches the water tap. By that time, the pollution may be very difficult to correct, and may even require new sources of safe water to be found, involving time, discernible inconvenience and considerable expense.

Most landfill is of domestic origin, but industrial, commercial, and military presence increases the likelihood of hazardous wastes being incorporated in landfill. For example, organic solvents which are used as degreasing agents for cleaning machinery are often detected as contaminants in groundwater.

As another example of contamination of groundwater, leaks from underground storage tanks used primarily for gasoline and other liquid petroleum fuels have had a significant adverse environmental impact in the United States. It has been estimated that there may be as many as 3.5 million underground storage tanks in the U.S. Estimates of the number of those tanks that are leaking tanks are already overwhelming, and the number is expected to continue to increase in the next few years. Many of the groundwater contamination incidents have been attributed to leaking storage tanks.

One of the primary causes of storage tank leakage is corrosion. It will be understood that product loss from the storage tanks by leaking will cause an adverse effect on the environment, endanger lives, reduce income, and require expenditure of millions of dollars in clean-up. A satisfactory system for accurately determining the presence of underground tank leakage is therefore desirable to prevent or reduce the adverse effects thereof.

Various volumetric, non-volumetric, inventory monitoring, and leak-effects monitoring detection methods and systems are known. Certain of these are described in patents which are discussed hereinafter.

Typically, monitoring and detection of groundwater contamination has involved the installation of wells, sample collection, sample preservation and laboratory analysis. These steps are expensive, time consuming, and often subject to error. Further, there is generally a considerable time lag between the identification of a problem and the measured initial results. The monitoring well becomes a permanent environmental change at the study location. Hence, these monitoring and detection methods are not conducive to screening studies in instances where problems are only suspected and many sampling locations are needed. Because groundwater pollution does not generally leave detectable physical evidence on the ground surface, the lack of such easily detectable evidence almost entirely eliminates simple forms of screening to discern potential problems or to further investigate suspected problems.

U.S. Pat. No. 4,709,577 issued Dec. 1, 1987 discloses apparatus and method for detecting leaks from underground gasoline storage tanks and the like. That invention, however, depends on the insertion of a particular tracer into the contents of the storage tank, and the routine or periodic soil samples taken from the soil outside the tank are tested for the presence of that particular tracer. The invention is limited in its application. First of all, it appears inapplicable to general exploration, for it is only practical to insert the particular tracer where an already known facility exists and is suspect. Secondly, knowledge gained from the test results appears restricted to the learning of the simple fact only that a leak has developed in that known facility.

U.S. Pat. No. 2,928,247 discloses a system and method of detecting leakage from an underground storage cavern. Analyzers are provided to sense any stored material which may leak from the underground cavern into an adjacent porous formation. Although this shows the concept of a porous layer being inserted between a leaking source and an analyzer sensor, it appears from this disclosure that the porous formation is relied upon only to slow the rate of leakage to a point to avoid exceeding the capacity of a nearby downhole pump for pumping liquid up to the surface to an analyzer located there.

U.S. Pat. No. 4,618,855 discloses a soil pollution monitoring system which is evacuated to draw air and vapor through sampling tubes that appear to be perforated. Air/vapor samples are contemplated in the operation. Any liquid in the system is considered an abnormality, and special compensation is therefore made for such liquid. The system is complex. Furthermore, it, too, is limited in its applicability.

West German Published Patent Application No. 1,804,441 discloses an underground tank leak detecting system using a pipe with perforated walls in which a second pipe or tube is located to extend along and beneath the tank. This is an oil leak warning system, and air is drawn through the pipe system to carry any oil fumes that might be present to a monitoring unit that in turn establishes the presence of the fumes. This is again limited to a permanent type installation and restricted in its detection ability.

Other known systems also detect volatile hazardous compounds in the environment and are based on instrumental techniques. These techniques may be classified with respect to sensitivity, specificity, and the complexity and sophistication of the instrumentation required. The more specific, sensitive methods often require expensive laboratory facilities, while less sensitive and less specific methods are carried out with relatively unsophisticated field apparatus. Some instruments are not very selective and are capable only of indicating an activity of some kind of volatile compound. Laboratory techniques such as gas chromatography/mass spectrometry may provide a quantification and identification of individual organic compounds from a single sample. Such techniques require the services of trained analysts, expensive instruments and laboratory settings. The least selective instruments include those commonly identified as portable organic vapor analyzers, while more selective laboratory techniques generally are based on chromatography and gas chromatography/mass spectrometry. The portable gas chromatograph is an example of an instrument that is intermediate these extremes.

The several categories of analytical instruments used for the detection of volatile hazardous compounds in the environment require differing techniques for sample introduction. A total analysis, of course, includes the obtaining and introducing of a sample as well as the chemical analysis of that individual sample. Accordingly, an overall analysis may be limited by instrument performance or by limitations imposed by the sample collection and introduction or both.

Instrumental techniques for analysis of organic compounds dissolved in water generally require the collection of a bulk sample of water. Furthermore, access to this water is generally gained by drilling into the subsurface environment and installing a sampling well. Sampling wells generally have an air-to-liquid interface between the well contents and the atmosphere, and dissolved volatile substances may escape from the well water to the atmosphere prior to sampling, potentially producing inaccurate samples. Surface active substances may also migrate to and accumulate at the air-to-liquid interface, producing another potential source of error. Typically, to minimize this problem several well volumes of water are pumped from a sampling well prior to sampling, but this may create turbulence within the well which enhances gas exchange. Moreover, the drawing of a sample from the well to the ground surface then becomes a problem, and specialized submersible pumps that minimize contact between sample and atmosphere in all probability should be added to the system, resulting in a more complex and costly system than desired. Furthermore, wells in and of themselves are costly and often sources of contamination. If the wells are abandoned, they leave the area in a permanent environmental change by their physical presence.

Simply stated, known methods of obtaining samples of groundwater that are representative of the contaminated conditions are not obtained at reasonable costs and without materially disrupting the environment. Furthermore, the known methods do not lend themselves to rapid or short term testing. Nor even do they lend themselves to the most satisfactory long term or permanent testing and observation. Accordingly, it appears desirable to provide a system and method that would overcome these drawbacks. Furthermore, it has been found that the content of water vapor in flue gases may be analyzed for the presence of contaminants, and so preferably the principles of such a method and system should also include the ability to detect contaminants in flue gases.

It has been proposed that for certain purposes it is not necessary to measure the concentration of a particular organic pollutant in the groundwater as such in order to obtain useful information on the general extent and direction of movement of a groundwater contaminant. In particular, it has been proposed that because the soil atmosphere in the zone above the water table, called the vadose zone, also becomes contaminated with volatile organic compounds by diffusion of organic vapors from the underlying water table, measurements may be made of concentrations of organic vapor in the soil atmosphere to delineate the extent of movement of contaminated water. This kind of sampling of the soil zone above the water table would involve minimal or no drilling which with an on-site analytical instrument, would involve handling of gases only. It would appear, therefore, that such sampling would be a cost effective field technique, particularly considering that portable gas chromatographs capable of being hand-carried to an otherwise inaccessible field site are available. This includes the field portable mass spectrometer, and this allows for on-site application of mass spectrometry. The mass spectrometer has the unique potential of being a versatile detector capable of providing a qualitative as well as a quantitative identification of unknown compounds.

In a known trial of this vadose zone sampling, however, too much effort may have been spent on obtaining successful sampling identification with field instruments of the mass spectrometer type. Thus, difficulties with the detector/analyzer segment of the sampling procedure brought an unsuccessful conclusion to the attempt. Moreover, known limitations to vadose zone sampling include the fact that concentrations in underlying groundwaters are not directly measurable by this technique. Such sampling will not reveal the actual degree of contamination of water at a particular depth of concern in an aquifer, and it does not appear suitable for the identification of contaminants which may lie deep within an aquifer. Thus it has appeared that a sampling well or other device is needed to reach the saturation zone itself, involving separate systems for vadose and aquifer testing. The sampling techniques, therefore, preferably should be capable of including subsoil gases, liquids and liquid masses with equal ease and without alteration. Furthermore, sampling to delineate aggression of under surface pollution preferably should include an array of sampling points, which in the previous known systems have been provided by wells.

Such techniques could greatly ameliorate a major problem in the cleanup process of, for example, landfill dump sites, which problem stems from a paucity of information regarding the dump site composition and aerial and volumetric extent. This lack of information has severely impacted all aspects of dealing with dump sites, i.e., remedial investigations and feasibility studies, hazard ranking, risk assessment, site remediation, etc. Performing a general prospecting survey of hazardous fluids including their mobility or stability at a given site is of significant value in developing preliminary overall containment and treatment plans. Thus, a network of relatively low cost implanted soil gas samplers deployed throughout dump site vadose and peripheral zones as well as adjacent aquifers and high permeability strata can be utilized effectively and is desirable for site prospecting. The concept of such an implanted sampler network, however, appears viable only if waste characterization data can be provided quickly and inexpensively and if the sampler can provide samples of all hazardous soil fluids and can interface at the dump site with a variety of analyzer/monitors and secondary samplers.

Accordingly, an urgent need exists for a rapid and relatively inexpensive instrumental method that is capable of obtaining and analyzing samples equally well from soil and from liquids and from an array of positions in either, to determine the existence and extent of under-surface contamination. Desirable characteristics for a solution include something that is relatively portable, easy to operate, and rapid in identification of contaminants.

SUMMARY OF THE INVENTION

In accordance with this invention, one described embodiment includes a system for detecting underground or underliquid contamination having probe means and membrane means within the probe means. When the probe means is put in a zone of a medium containing a contaminant, whether that medium be soil or liquid, such as water, the probe means will obtain a fluid sample, which sample will be used for detecting the presence of the contaminant. This sample is obtained by collecting the substance that passes through the membrane means, hereinafter referred to as the diffusate, from the medium being tested and internally delivering it to a test position. Accordingly, the system includes conduit means that extends from the test position outside the medium to the probe means in the medium and then separately returns from the probe means to the test position. The system also includes supply means at the test position connected to the conduit means for injecting a carrier gas in the system to mix with and to transport the diffusate from the probe means to the test position. A detector/analyzer means is also located at the test position and is connected to the return conduit means and receives the transported carrier gas/diffusate mix for detecting the presence of and analyzing the diffusate.

The system operates equally well for testing fluid contamination in soil or in liquids and is useful for establishing an array of test points, either temporary or permanent, in the test zone to monitor and analyze the extent of and migration patterns of the fluid contamination. Initial prospecting of a dump site to explore its general extent and composition is prudent prior to extensive mapping and characterization. The subsurface mobility of hazardous and other fluids can be tracked with a two or three dimensional network of the systems deployed in the peripheral zone of a dump site or within the vadose zone as dictated by monitoring strategies.

To simplify the illustrations and description, however, the invention will be shown and described herein primarily in relation to soil testing.

DESCRIPTION OF THE DRAWINGS

Advantages and features of this invention will become apparent by reference to the following specification and to the accompanying drawings, in which.

DETAILED DESCRIPTION

Although the invention is described herein primarily in connection with a preferred embodiment, it should be understood that it is not intended to limit the invention to the embodiment described. On the contrary, it is intended to cover all alternatives, modifications and equivalents as may be included within the spirit and scope of the invention defined by the appended claims.

Figure 1:
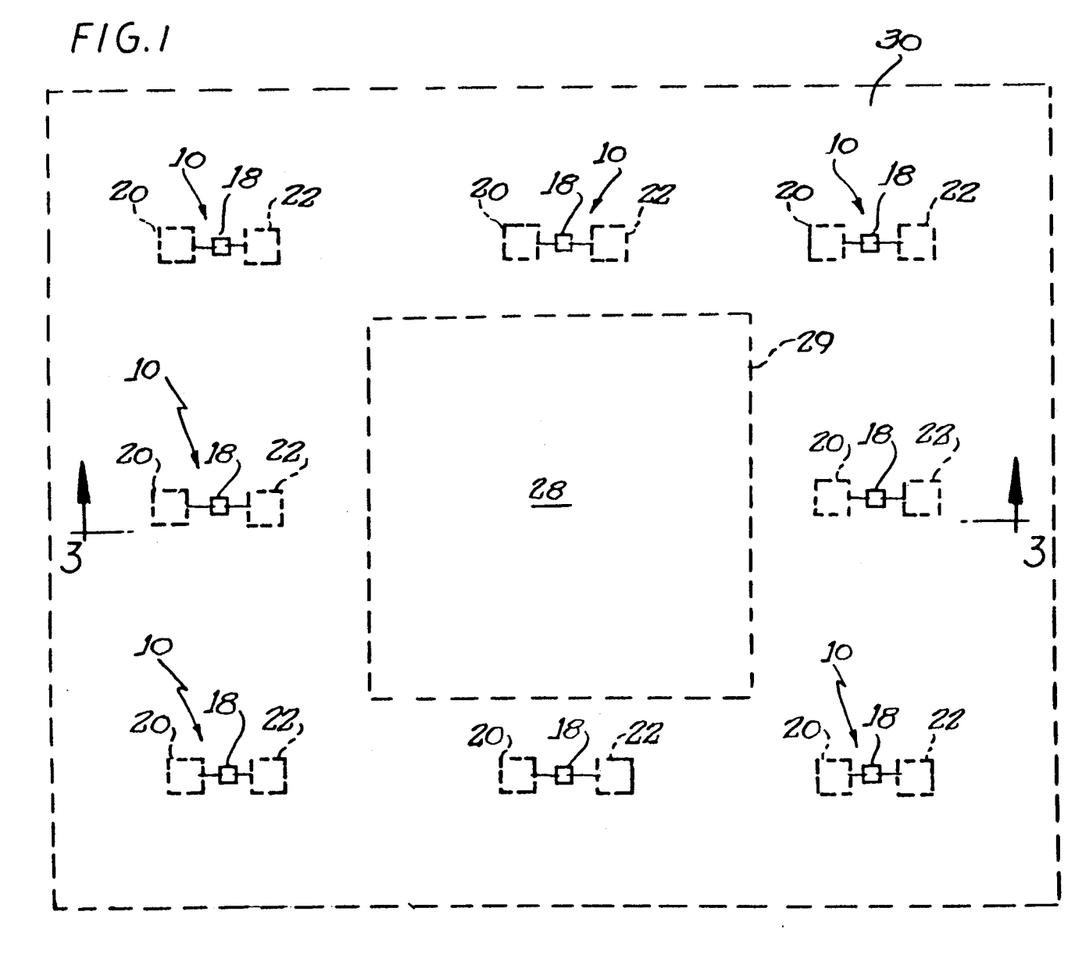
FIG. 1 is a plan view of a zone in the earth to be tested and including an array of sampling devices according to the invention laid out in an arbitrarily selected (for purposes of illustration) two-dimensional pattern for detecting and analyzing the zone for contaminants.
Figure 2:
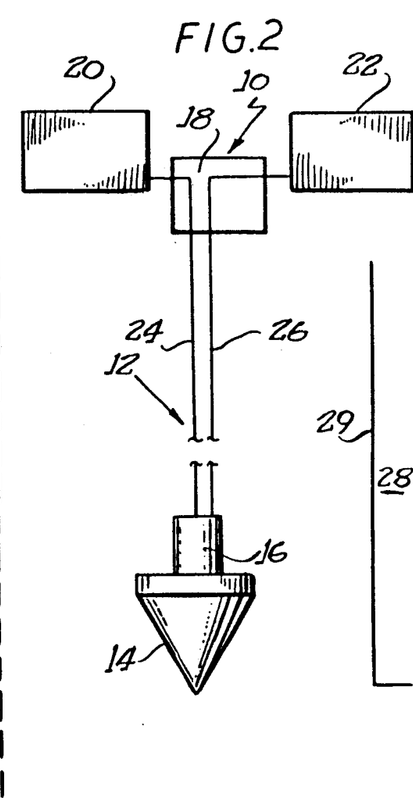
FIG. 2 is a diagrammatic depiction of a system for detecting subsurface contamination according to the invention.

Briefly, as shown in FIGS. 1 and 2 for purposes of illustration, the invention is embodied in a system 10 for monitoring and analytically measuring subsoil gases and liquids and liquid masses for concentration of contaminants and impurities. The system 10 also avoids the need to separately collect individual samples for removal to a remote laboratory.

The system includes an implant or probe 12 capable of sampling soil gases and liquid vapors without drilling a well. The soil gases and liquids are sampled by the implant which can be driven into the soil and left for either a limited time or permanently for testing. The probe includes a penetrating head 14, which may be the tip of a cone penetrometer, that opens a path for a membrane module 16. As will be seen hereinafter, this membrane module 16 includes an assembly of concentric tubes which are porous and gas permeable and which are placed in subsurface levels for receiving a diffusate therethrough from the surrounding medium.

Located at the surface of the medium is an interface module 18 having at least pneumatic connections. Connected to the interface module 18 is a supply device 20 for a carrier gas and a device 22 for monitoring and analyzing the diffusate.

The probe 12 communicates pneumatically with the surface interface module 18 through two substantially parallel lines of small diameter conduits or tubes, a supply tube 24 and a return tube 26. The supply tube 24 leads from the carrier gas supply device 20 to the membrane module 16, and the return tube leads from the membrane module 16 to the monitoring and analyzing device 22. A stream of carrier gas flows under controlled conditions from the interface module 18 to the membrane module 16 through the supply tube 24 and lifts the diffusate that enters the membrane module 16 to the surface through the second tube 26 for subsequent monitoring, analysis, secondary sampling, or further processing. As will be described later, a secondary sampler, for example, a grab bag, can be attached directly to the interface module or downstream of the gas analyzer/monitor. Soil gases flow into the implant at a rate directly proportional to the soil gas species partial pressure and inversely proportional to the implant soil gas diffusion impedance.

The system 10 is shown in FIG. 2 adjacent an underground storage facility 28, such as a tank, landfill, or hazardous waste dump site. Unless the underground storage facility is a tank, there may be a liner 29 provided for containing or limiting the underground storage facility. This liner may be in the form of a rock or other naturally occurring barrier, or it may be man-made.

A plurality of systems 10 can be deployed in an array to depths that are sufficient for sampling the entire vadose zone of a dump site and at deeper depths around the peripheral zone of the site. Thus, an array of systems can take a three dimensional form as well as a two dimensional form. FIG. 1 shows the underground storage facility 28 with an array of systems 10 deployed in a two dimensional form to surround the facility within a determined zone 30. As will be seen hereinafter, the plurality of systems 10 are deployed in the array with a probe extending into the medium from the interface module 18 at each location in the array as shown in FIG. 2. The modules 18 are connected to each subsurface probe in the array and left in place for further connection of both the carrier gas supply device 20 and the monitoring device 22. These devices can be connected to one system at a time at periodic intervals around the array and the tests recorded so that subsequently a plot of the recordings would reveal the nature, extent, and migration of a contaminant within the test zone. Alternatively the various positions in the array can be monitored continuously and the results plotted at more frequent intervals by providing sufficient devices 20 and 22 for permanent connection to the respective interface modules.

Figure 3:
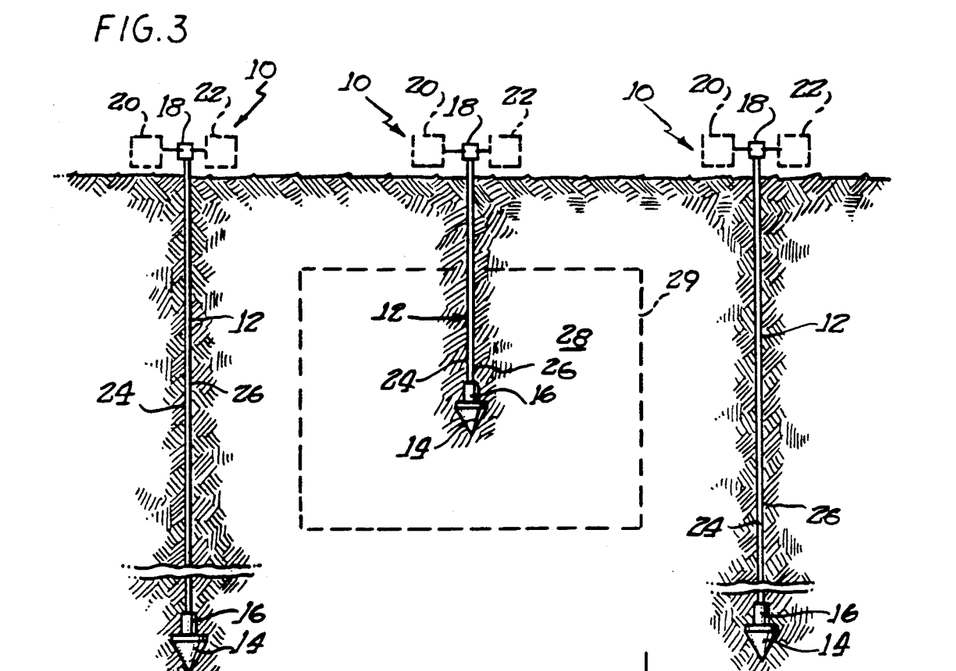
FIG. 3 is a sectional view taken along the line 3—3 of FIG. 1 showing a few of the sampling devices in the array at different depths and illustrating a third-dimensional aspect of the array according to the invention.

FIG. 3 illustrates the three-dimensional aspect of the invention wherein the systems 10 can be deployed at various depths so as to sample the regions at the ends of, above, below, at the sides of, and otherwise around the peripheral zones of the site.

The system 10 includes the following features and advantages:

a. Simple, low cost sampler deployment;
b. Minimal soil disturbance from deployment;
c. Minimal sample extraction during each sampling episode, providing a correspondingly more representative sample of soil gases;
d. Minimal hardware;
e. Small dimensions of the hardware; and
f. Sample obtained is independent of soil gas permeability, soil porosity and gas viscosity.

In connection with feature (e), a small sampler module has concomitantly smaller transverse dimensions, which allow for a proportionally easier deployment of the system. As is described hereinafter, the implant may be about 1 inch (2.54 cm) in the transverse dimension, and it can be deployed by means such as commercially available cone penetrometers. An important consideration of using implants for the initial prospecting process and then progressing to the characterization and monitoring phases is that a network of permanent implants is then available from the time of the initial prospecting, which provides utility thereafter for the life of the dump site.

Summarizing this brief description of the invention, it can be seen that the system 10 includes two modules: the subsurface implant 12 and the surface interface module 18 with associated devices for connection therewith. Soil gases enter the implant 12 at flow rates proportional to the individual gas partial pressures and the partial and vapor pressures of dissolved and pure liquids, respectively. The soil gases are lifted to the surface by the carrier gas stream which enters the interface at the surface and flows at a controlled and measured flow rate down through the implant and then returns to the surface. Soil gas analysis and monitoring is accomplished by the analyzer/monitor 22 attached to the carrier gas stream return line 26 at the interface. The analyzer/monitor 22 and carrier gas used can be selected to be compatible with all aspects of the system 10 when considering the data quality requirements of the application. Carrier gases that may be used, for example, are helium and dry nitrogen. As will be seen, a secondary sampling device, such as a grab bag or bubbler, may be attached to the interface, and soil gas may be collected in batches for subsequent laboratory analysis. With a sufficiently large carrier gas stream flow rate, one or more analyzer/monitors and/or one or more secondary samplers can be attached to the carrier gas outlet of the interface and can be operated concurrently.

Figures 4, 5, 6:
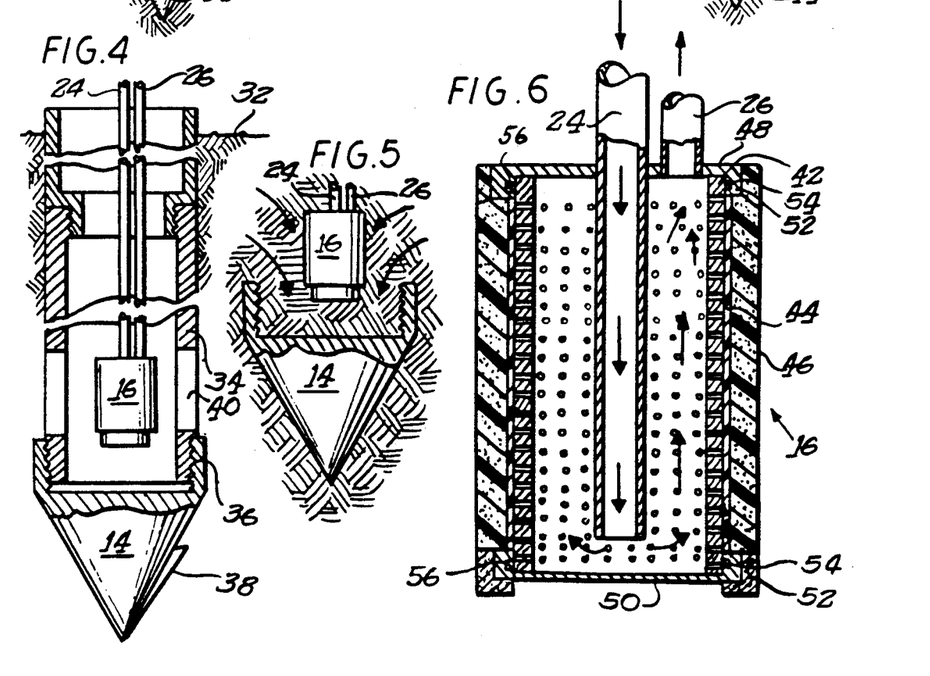
FIG. 4 is an enlarged cross-sectional view of a probe utilized in the system of FIG. 2.
FIG. 5 is a view of the probe as in FIG. 4 except with the shaft withdrawn from the earth, leaving the cone tip, the membrane module and conduits in place and the soil collapsed therearound.
FIG. 6 is an enlarged cross section with dimensions not in proportional relationship of a semipermeable membrane module for use in the probe of FIG. 4.

More specifically, FIG. 4 is an enlarged cross-sectional view of a probe 12 utilized in the system 10. As illustrated in FIG. 4, the probe 12 is deployed in a medium 32 illustrated as earth. As already mentioned, however, this probe operates equally well in liquids as in soil. In one instance the molecules of vapor enter the membrane, as will be seen hereinafter, on one side in a gaseous phase and depart on the other side of the membrane into another gaseous phase; whereas in the other instance the molecules of vapor enter the membrane on one side from a liquid phase and are released to a vapor phase on the other side of the membrane. Thus, the subsurface could represent a liquid medium, such as the contents of a well. The medium also could be the earth with the probe extending into an aquifer. For purposes of illustrating and describing this embodiment, however, the medium 32 is indicated as earth with the probe 12 extending downwardly into soil. It should be understood, however, that there is no intention of limiting the invention to use in soil. On the contrary, the invention is useful in liquids and liquid masses as well as in soil.

Quite often environmental concerns center around leaks from underground gasoline storage tanks. One of the primary causes of tank leakage is corrosion of such storage tanks. Product loss from leaking tanks may cause an adverse effect on the environment, as well as endanger lives, reduce income, and require considerable expenditure for cleanup. If, therefore, the subject to be tested concerns a zone in which a storage tank is contained, the probe 12 need be only long enough to extend a few feet under the surface of the earth. On the other hand, there may be instances where it is desirable to test in situ the soil in an aquifer or other soil medium in a considerably deeper location than required for an underground storage tank. Thus, it is desirable for the structure of the probe 12 to include means for extending it to depths of up to 100 feet (30 meters) into the earth. It is known, for example, in oil drilling rigs that sections of pipe (called spaghetti when hung out on racks on an oil derrick) are joined end to end to extend a drill bit down into the depths of the earth. A similar provision is made here for forcing the probe 12 into the earth.

In this connection, FIG. 4 shows a driving head or cone penetrometer 14 which is in the form of an inverted cone with its outer surface acting as a plow as it is driven into the earth. The cone tip may be considered expendable with only provision made for retrieving the shaft. Once the assembly has been driven down into the earth, therefore, the shaft can be removed, leaving the cone 14, the membrane module 16, and the connecting lines 24 and 26, as illustrated in FIG. 5. On the other hand, instances may occur in which it is desirable to leave the shaft in place with the implant. An opening 40 is provided in the shaft segment that contains the membrane module 16 so that fluids surrounding that portion of the probe can migrate into the module 16. Leaving the shaft in place, of course, also supports the integrity of the implant if it is left for permanent installation in the site. More than one opening 40 may be provided, and the opening may further include a screen covering or louver (not shown).

Referring in more detail to the shaft, FIG. 4 illustrates a shaft 34 which may be provided in sections of convenient lengths with means at the end of each section for joining end to end with another section at a joint 36. This joining may be accomplished in any known manner, such as by one end of each shaft segment being threaded externally and the other end being threaded internally to receive the externally threaded end of another segment in a complementary manner. The segments may be any convenient length, for example 10 feet (approximately 3.3 meters). The normal right hand threading may be used for all segments except for the end that engages the cone 14. This threading should be opposite so that none of the shaft segments will unscrew if it is desired to disengage the shaft from the cone. Disengagement of the shaft 34 from the cone 14 may be effected in the illustrated structure by rotating the shaft 34 in a direction reverse to that of the threading direction so as to unscrew the shaft from the cone. Of course, the cone will have a tendency to follow the rotation of the shaft, but the friction of the surrounding soil will help to prevent it. The non-rotative condition of the cone 14 may be enhanced, however, by, for example, the addition of at least one fin 38 (FIG. 4) longitudinally on the face of the cone. More than one such fin may be provided at equal or unequal intervening intervals around the face of the cone. It is assumed in this structure, of course, that the means for driving the probe 12 into the earth will be a downwardly driving force on the shaft 34 from the surface and not a rotative or drilling force. The standard practice for inserting cone penetrometers can be adopted.

Referring now to FIG. 6, the cross-sectional illustration of the implant 12 shows an array of four concentric tubular elements; namely, the supply tube 24, the central-most tube; a support tube 42; a membrane tube 44; and a protector tube 46, the outermost tube. The central supply tube 24 introduces carrier gases into the implant.

Preferably, this supply tube is made of a material, such as Teflon or high quality stainless steel, that is inert to soil conditions. The perforated metal tube 42, which may be also of stainless steel, is a thin-walled tube that provides mechanical support for the tubular membrane. The outermost tube 46 is a porous padding, such as a polymeric padding material, that provides the tubular membrane with protection from soil abrasion, etc., in the event of soil movement past the implant. The centrally positioned supply tube may be a ¼-inch (6.4 mm) outside diameter tube. The thin-walled perforated metal tube 42 may be a ⅞-inch (22 mm) diameter perforated metal tube. The tubular membrane 44 may be a 0.001-inch (0.025 mm) thick Teflon tubular membrane. The protector tube 46 may be a ⅛-inch (3.2 mm) thick tube of a porous polymeric padding material.

The assembly is sealed at each end by a top cap 48 and a bottom cap 50, respectively. Both these caps are preferably made of metal. These caps each include a peripheral skirt portion 52 that clamps the cap in a press fit condition over the respective ends of the support tube 42. The peripheral skirt portion includes a slot 54 which purpose is to contain an O-ring for sealing the tubular membrane 44 to the head end and foot end respectively of the perforated support tube 42. The tubular elements in the embodiment shown are approximately 6 inches (15.24 cm) long, and the outer diameter of the entire concentric tube assembly is approximately 1 inch (2.5 cm).

The top cap 48 has provision for receiving the supply tube 24 for the carrier gas stream through the cap, and for the return tube 26, which may be also of stainless steel, to also extend through the cap. The bottom cap 50 with the O-ring 56 seals the tubular membrane 44 at the opposite or bottom end of the implant.

Figures 7, 8, 9, 10:
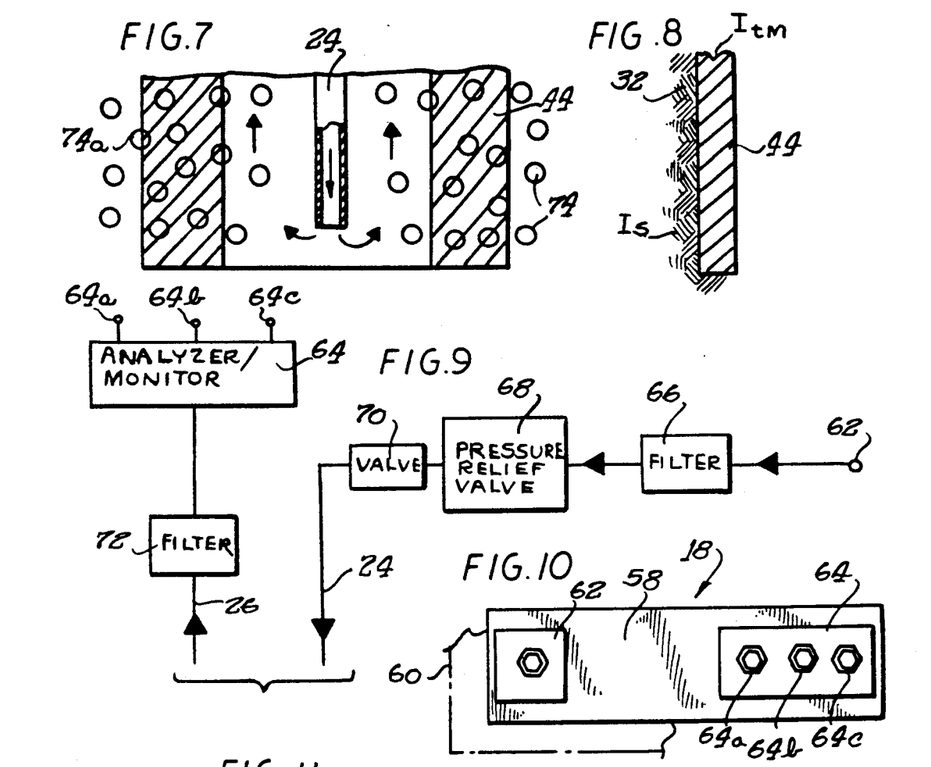
FIG. 7 is an enlarged segment of the semipermeable membrane of the module of FIG. 6 and illustrating molecules passing through the membrane and being immediately swept away by a carrier gas.
FIG. 8 is a depiction of total impedance to diffusion from a medium such as soil particles on the left through an adjacent membrane as used in the invention.
FIG. 9 is a schematic diagram illustrating a pneumatic circuit of the system of FIG. 2.
FIG. 10 is a plan view of an interface module for use in the system of FIG. 2.

Referring now to FIG. 10, the interface module 18 comprises a pneumatic panel 58 contained in a weather proof housing 60 (shown only as a representation and not in detail) mounted to a stake (not shown) imbedded in the soil. A gas connection 62 is made through a fitting that leads to the carrier gas supply 20 on the one side and to the supply line 24 to the implant 12 on the other side. The carrier gas return line 26 from the implant connects to a manifold 64 for further connections on the other side to the analyzer/monitor 22 and/or secondary sampling devices (shown as 78 in FIG. 11). All gas connections are made at the face of the respective connection panels as illustrated. Reference Nos. 64a, b and c, refer to the analyzer/monitor and secondary sampler connections.

An interface pneumatic network is illustrated schematically in FIG. 9. The carrier gas connection 62 is shown at the far right in the figure, and this represents the point at which the carrier gas is inputted from the supply device 20. The pneumatic lines 24 and 26 are provided with in-line filter cartridges. Furthermore, the carrier gas line 24 includes an in-line pressure relief valve and a shutoff valve to prevent over pressurization of the implant and to assist in the startup and checkout processes. Therefore, beginning at the right side in the FIG. 9 at the connection 62, the carrier gas proceeds downstream to a filter 66 on the input side of the system, thence, to a pressure relief valve 68 and finally to a shutoff valve 70 before continuing downstream to the implant 12 in the supply line 24. After the carrier sweeps the membrane module 16 and mixes with the diffusate for the return trip in line 26 to the surface, the carrier gas/diffusate mix passes through a filter 72 before it reaches the manifold 64 for distribution to the analyzer/monitor 22 and/or sampler devices.

When not in use, the ports are capped or plugged. It should be noted that no electrical power is required to either maintain or operate the interface module 18 or the implant 12 as described. All power requirements are associated either with the flow control network and carrier gas supply 20 or with the analyzer/monitor 22.

Before examining in detail the principle of operation, reference is made to FIGS. 7 and 8.

FIG. 7 illustrates the diffusion process by showing the membrane tube 44 along with the supply line 24 and a few sample molecules 74. The sample molecule 74A on the outside of the tube collides with the tube wall surface. The sample molecules then dissolve in the tube wall and diffuse into the interior of the tube where the carrier gas from the input line 24 sweeps up the molecules and carries them in the return line 26 to the surface. The membrane tube 44 is preferably of a semipermeable material, and the molecules 74 that dissolve or diffuse through the wall become the diffusate that forms the sample to be tested on the surface.

FIG. 8 illustrates the total impedance to the sample gas flow from the soil through the tube wall to the tube interior. The impedance to soil gas flowing from the soil into the implant interior is composed primarily of (1) the soil gas impedance and (2) the tubular membrane diffusion impedance in series as illustrated in FIG. 8; i.e., $$I_T = I_{tm} + I_s$$

where $I_T$ = total gas flow impedance from surrounding soil into the implant, torr-min/cm$^3$;

$I_{tm}$ = tubular membrane impedance, torr-min/cm$^3$; and $I_s$ = soil gas impedance, torr-min/cm$^3$.

It has been found that if the membrane module 16 is constructed such that $$I_{tm} >> I_s \text{ and}$$

$$I_T \approx I_{tm}$$

the soil sample flow rate will be dependent primarily on $I_{tm}$ and, consequently, will be independent of $I_s$. Therefore, because $I_s$ is a function of soil permeability to the soil gas and soil gas viscosity, the sample flow rate is independent of the soil conditions and gas viscosity in the construction according to the invention, and it is dependent primarily on the properties of the tubular membrane 44 which are both known and controllable. Hence, because of the controllable properties, the tubular membrane 44 is an important element in this invention. As shown below, the soil gas concentration measured at the interface 18 can be related directly to the soil gas concentration or partial pressure.

Referring now to the overall operation of the system, as already indicated, implant operation is based on a flow of soil gases by diffusion through the semipermeable tubular membrane 44 and into the interior of the module 16. As carrier gas flows through the module 16 of the implant 12, the concentration of the soil gas species in the carrier gas stream at the interface module 18 is a ratio of the two gas flow rates:

$$[G] = (Q_s/Q_c) \, 10^9 \tag{1}$$

where $[G]$ = soil gas species concentration in the carrier gas stream at the interface module, parts per billion (ppb);

$Q_s$ = soil gas species flow rate into the implant, std. ml./min.; and $Q_c$ = carrier gas flow rate, std. ml./min.

The soil gas species flow rate into the implant 12 is related to the soil gas species partial pressure or concentration in the soil by the permeation conductance of the implant 12:

$$Q_s = K(P_{sg} - P_{ig}) \tag{2}$$

where $K$ = implant soil gas species permeation conductance, std. ml./min.-torr;

$P_{sg}$ = gas species partial pressure in the soil, torr; and $P_{ig}$ = soil gas species partial pressure in the implant or in the carrier gas stream at the interface, torr.

$K$ is specific to the soil gas species and the tubular membrane material:

$$K = 2\pi L P_m / \ln(r_o/r_i) \tag{3}$$

where $L$ = implant tubular membrane length, cm.:

$P_m$ = implant tubular membrane permeability coefficient of the soil gas species, std. ml./min.-cm.$^2$-torr/cm.;

$r_o$ = implant tubular membrane outside radius, cm.; and $r_i$ = implant tubular membrane, inside radius, cm.

$K$ will be determined by in situ calibration or in the laboratory.

The soil gas partial pressure in the soil is related to measured and calibrated parameters by combining equations (1) and (2):

$$P_{sg} = 10^{-9} (Q_c/K + P_c) \, [G] \tag{4}$$

where $P_c$ = carrier gas pressure at the interface, torr.

By lumping the consistent and measured and calibrated parameters into the term, y, equation (4) is simplified to:

$$P_{sg} = y \, [G] \tag{5}$$

The entire system will respond reasonably fast. There are two aspects of response time: (a) the time to saturate the tubular membrane with soil gas to an equilibrium concentration, and (b) the carrier gas lag time in the pneumatic lines. The response time of the implant membrane to 99 percent of equilibrium for a step change in soil gas concentration is described by:

$$T_s = 5(r_o^2 - r_i^2) \ln(r_o/r_i)/2D \tag{6}$$

where $T_s$ = implant membrane response time to 99 percent, sec., and $D$ = implant membrane soil gas species diffusion coefficient, cm.$^2$/sec.

For an implant with a 0.785-inch (20 mm) Teflon tubular membrane 0.001 inch (0.025 mm) thick, and a soil gas diffusion coefficient of $10^{-6}$ cm.$^2$/sec, the implant response time to reach equilibrium will be approximately 38 seconds. The lag time will depend on the inside diameter of the carrier gas pneumatic lines and the depth of the implant. For the system 10 operating with a 30-std. ml./min. carrier gas flow rate stream, 0.030-inch (0.76 mm) inside diameter pneumatic lines, and an implant 100 feet (30 m) below the surface, the lag time of the system will be 56 seconds. The total response time of the system 10 to a step change in soil gas partial pressure will be approximately 94 seconds.

Equations (1) and (2) describe the soil gas species concentration at the interface for the system 10 operating in the dynamic sampling mode, i.e., the operating mode in which the carrier gas flows continuously through the implant. The implant can also, however, be used in the static sampling mode, i.e., the operating mode in which the carrier gas does not flow ($Q_c=0$) for a prescribed period of time preceding dynamic sampling. The soil gas flow in the implant will continue, regardless, until the soil gas partial pressure difference across the tubular membrane is zero as described by equation (2). At this point, the net flow of soil gas into the implant is zero, and an equilibrium soil gas concentration is obtained, i.e., $P_{sg}=P_{ig}$. Thereafter, the system 10 operation in the dynamic sampling mode is resumed, and the soil gas species accumulated in the implant are lifted to the surface.

The soil gas partial pressure, $P_{ig}$, measured at the interface module 18 in the static sampling mode will be less than soil partial pressure, $P_{sg}$, because of mixing and subsequent dilution of the soil gas accumulated in the implant 12 by the carrier gas stream. It is estimated that five implant volume exchanges with carrier gas will be required to remove the soil gas from the implant. Assuming homogeneous mixing, the average soil gas concentration or partial pressure measured at the surface will be one-fifth the soil gas partial pressure during the five volume gas exchanges. At a carrier gas flow rate of 30 std. ml./min., the time period is approximately 10 minutes.

For the initial condition, $P_{ig}=0$, the time required to obtain the static equilibrium condition, $P_{sg}=P_{ig}$, is approximated by $$T_v = 5 \, V_s \ln(r_o/r_i) / 2\pi L \, P_m \, P_c \qquad (7)$$

where $T_v$ = time required for the implant internal soil gas partial pressure to attain equilibrium for the static sampling mode, min., and $V_s$ = implant internal volume, ml.

For the implant dimensions given earlier and a soil gas permeability coefficient of $2\times 10^{-9}$ std. ml./min.-cm.$^2$-torr/cm. for a Teflon tubular membrane, $T_v = 929$ min. or 3.22 days.

In situ calibration of the implant may be performed with calibration gas supplied to the external surface of the tubular membrane 44. In this connection, FIGS. 11, 12, 13 and 14 show a further embodiment of the system 10. For description of this further embodiment, like elements will carry the same respective reference numbers as earlier. Elements that are basically the same but modified in the embodiment are the respective earlier numbers raised by 100. Elements not previously described, of course, will carry newly assigned reference numbers.

Figure 11:
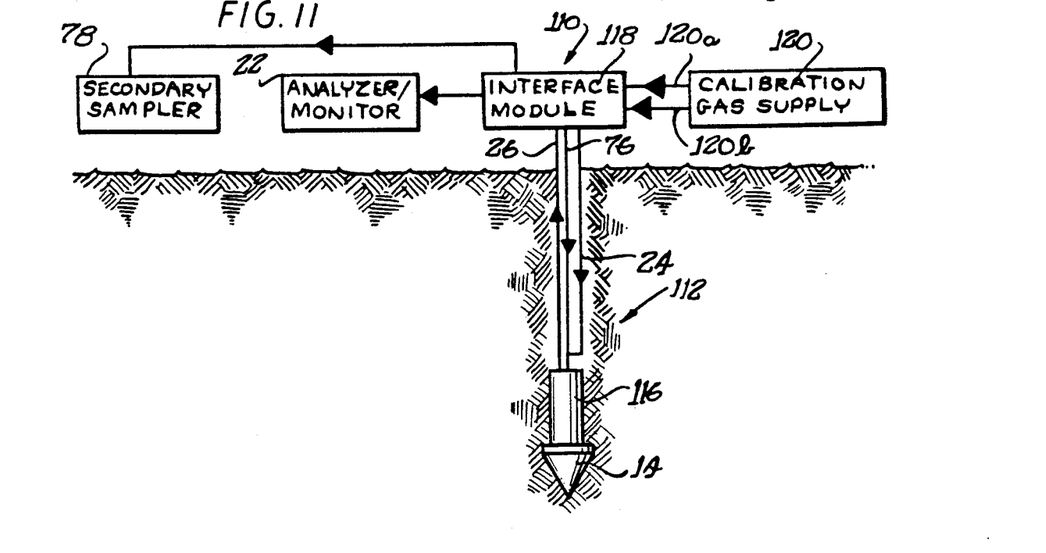
FIG. 11 is a diagrammatic depiction similar to FIG. 2 except of an alternative embodiment of the system according to the invention.

Referring first to the structure of the embodiment, FIG. 11 shows a system 110 which differs from the system 10 primarily in that means for operational check out and calibration of the system in situ is included as an integral part of the system. In FIG. 11, the interface module 118 receives input from a supply device 120 for calibration gas in addition to the carrier gas along with a control network. The schematic shows two lines with arrows extending from the supply device 120 to the interface module 118. One of the lines, 120a, represents the carrier gas input and the other of the lines, 120b, represents the calibration gas line. There are three lines that extend downwardly into the earth from the interface module 118. The supply line 24 and the return line 26 are provided as before. The supply line 24, however, joins a third line, a calibration gas line 76, at or near the entrance of the line into the membrane module 116. The cone 14, again, is used in driving the implant 112 into the medium to be tested, the earth or soil in this instance. FIG. 11 also shows an analyzer/monitor 22 and an auxiliary or secondary sampler 78 connected to the interface module 118 on the return side of the system.

Figure 12:
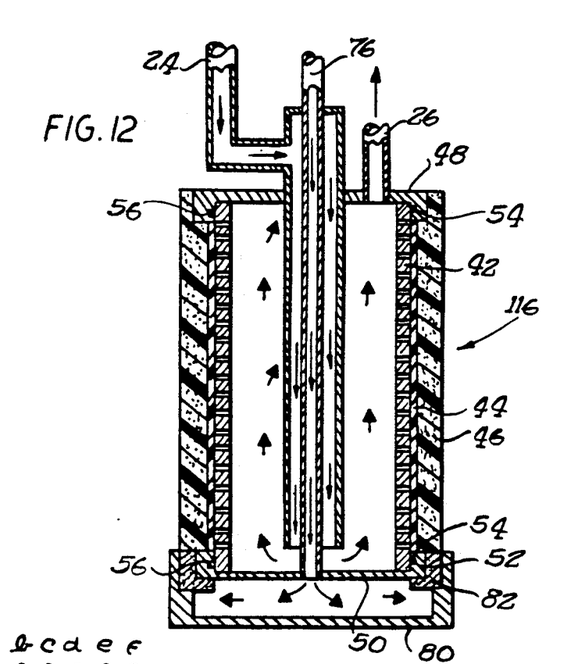
FIG. 12 is an enlarged cross section with dimensions not in proportional relationship similar to FIG. 6 except of an alternative embodiment of the semipermeable membrane module for use in the system of FIG. 11.

FIG. 12 shows a detail of a membrane module 116 for use in the system 110. Thus, the cross-sectional illustration of the implant 112 shows an array of five concentric tubular elements. Again, the assembly is approximately six inches (15.24 cm) long, and is contained within a one-inch (2.54 cm) diameter envelope. The assembly is sealed at each end by top and bottom caps 48 and 50, respectively. The two innermost tubes are approximately a 1/16-inch (1.6 mm) and a ¼-inch (6.4 mm) outside diameter metal tubes that introduce calibration and carrier gases to the implant as shown. The calibration gas comes through the centermost tube 76, and the carrier gas comes from the tube 24 that joins and surrounds the tube 76 and leads the carrier gas into the interior of the membrane module for sweeping the interior and eventually making its exit through the return line 26. These carrier gas and calibration gas tubes are surrounded sequentially by a ⅞-inch (22 mm) diameter thin-wall perforated metal tube, which is the support tube 42 as previously described; a 0.001-inch (0.025 mm) thick Teflon tubular membrane, which is the membrane tube 44 as previously described; and a ⅛-inch (3.2 mm) thick tube of a porous polymeric padding material, which is the protector tube 46 as previously described. Mechanical support for the tubular membrane 44 is provided by the perforated tube 42, and the porous padding 46 provides the tubular membrane 44 with protection from soil abrasion, etc., in the event of soil movement past the implant, as previously described.

The top cap 48 is a metal circular plate with a thick lip or peripheral skirt portion 52. The peripheral skirt portion includes a slot 54 for containing an O-ring 56 which seals the tubular membrane 44 to the header end of the perforated support tube 42. A concentric tube assembly for input of calibration gas and carrier gas plus a single ¼-inch (6.4 mm) outside diameter tube, the outlet for the carrier gas stream in the return line 26, penetrate the cap. At the opposite or bottom end of the membrane module 116, the bottom cap 50 with its O-ring seals the tubular membrane 44. Below that, however, a further flat-bottom cap 80 is provided overall on the outside of the bottom of the assembly. This additional flat bottom cap 80 also has a peripheral lip, which, however, is no thicker than the bottom wall of the cap. This further flat-bottom cap 80 provides an assembly essentially of two shallow cylindrical flat bottom caps fitted into one another, but separated by a further ring, namely a porous metal ring 82 inserted between the two lips of caps 50 and 80 as shown, defining a chamber between the two caps. The O-ring 56 is compressed by the bottom cap 50 to seal the tubular membrane 44 to the perforated tube 42 bottom header in a manner similar to that of the top cap 48. The chamber created at the bottom of the assembly between the caps 50 and 80 receives the calibration gas which enters the chamber from the calibration tube 76. The calibration gas tube 76 penetrates the inner bottom cap 50 and allows the calibration gas to flow into the chamber to the outer peripheral edges. From there, the calibration gas flows through the porous metal ring 82 to the area surrounding the outer wall of the membrane tube 44 where it will diffuse through the membrane tube 44 wall and be swept up internally of the tube by the carrier gas in a manner the same as for other diffusates.

Figure 14:
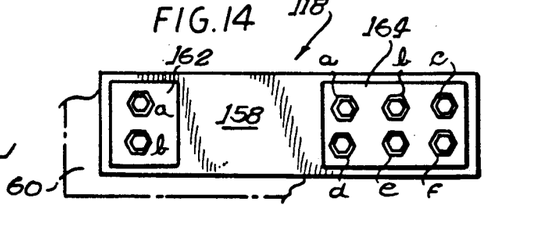
FIG. 14 is a plan view of an interface module for use in the system of FIG. 11.

FIG. 14 shows the interface module 118 that includes a pneumatic panel 158 in a weatherproof housing 60 mounted to a stake (not shown) embedded in the soil. Gas connections 162a for the carrier gas and 162b for the calibration gas are made through fittings that lead to the carrier and calibration gas supplies respectively from the supply device 120 on the input side and to the respective pneumatic lines 24 and 76 leading to the implant 112 on the other side of the connection. The carrier gas return line 26 connects to a manifold 164 for an analyzer/monitor device 22 and/or for secondary sampling devices 78 (FIG. 11). Connections 164a, b, c, d, e, and f are provided for these analyzer/monitor and/or secondary sampling devices.

All gas connections are made at the face of the connection panel as illustrated in FIG. 14. The interface pneumatic network for this further embodiment is illustrated schematically in FIG. 13. As described earlier, all pneumatic lines at entrances and exits contain in-line filter cartridges. The carrier and calibration gas lines each contain in-line downstream pressure relief and shutoff valves to prevent overpressurization of the implant and to assist in the startup and checkout processes. These in-line elements in the carrier and calibration streams are mounted to the backside of the connection panel. Thus, in FIG. 13, beginning at the right-hand side, 162a is the connection from the carrier gas supply device 120, and 162b is the connection for the calibration gas from the supply device 120. Each one of these lines proceeds downstream into filters 66, thence to pressure relief valves 68 and finally through shutoff valves 70 before proceeding downwardly to the implant 112. After entering the membrane module 116 of the implant 112 and sweeping the interior thereof, the carrier gas exits the module and proceeds back to the surface through the return line 26 and through a filter 72 before reaching the manifold 164. At that point, connections are made to the attached device 22 for monitoring/analyzing the carrier gas/diffusate mix and various secondary sampler devices 78 as may be connected.

When not in use, all ports are capped or plugged. Again, it should be noted that no electrical power is required to either maintain or operate the interface module 118 or the implant 112 as described. All power requirements are associated either with the flow control network and carrier gas supply device 120 or with the analyzer/monitor 22.

Returning now to a detail of the operation of this further embodiment, the operation described in connection with the system 10 applies also to the system 110. Additional description, however, is needed for the calibration gas stream. Accordingly, a calibration gas stream enters the calibration gas inlet 120b, flows through the calibration gas tube 76 and into the space or chamber between the bottom caps 50 and 80. The calibration gas continues to flow through the porous metal ring 82 to the external surface of the tubular membrane 44. The implant 112 operates on the calibration gas as it does on soil gas, i.e., $P_{sg}$ of equation (5) is supplied by the calibration gas. [G] is adjusted to maintain the equality after changes in y.

Aside from fundamental system analytical and monitoring interfacing performance specifications, the implant structural constraints may be established by reliability and service life requirements and deployment flexibility. Operational constraints may be associated with special-purpose operating conditions and interfaces conducive to obtaining the system performance specifications.

The systems 10 and 110 reliability correspond generally and most importantly to the exigencies of maintaining the relationships of soil gas species partial pressure, $P_{sg}$, and the measured soil gas species concentration, [G], described by equation (4). Adherence to this relationship is predicated on the design and operational integrity of the tubular membrane 44 and the pneumatic lines leading to the surface.

It is important that the soil gas flows into the implant by diffusion only. Consequently, the implants 12 and 112 are designed to ensure gas-tight seals. The tubular membrane 44 should be free of tears, punctures, and pin holes to ensure that the soil gas flows into the implant only as described by equation (2). Thus, pre-assembly inspection of the tubular membrane is important as is post-assembly inspection and leak and span checks. The tubular membrane 44 should not be damaged during the deployment and operational processes.

Preferably, relatively inert implant fabrication materials are used, because after deployment every external and perhaps some internal component or surface is exposed to chemical and physical attack. It is of prime importance that the tubular membrane material be inactive chemically and physically with the soil as well as with benign and hazardous soil fluids. Such condition will ensure that the tubular membrane material K remains unchanged during the life of the implant. Teflon of any form is a preferred material for the tubular membrane 44.

A simple but very important aspect in extending operating service life of the implant 12 or 112 is to ensure that the pneumatic lines from the interface to the implant are internally always clear of debris to minimize possible plugging. The filter cartridges 66 in the interface pneumatic network shown in FIGS. 9 and 13 assist in preventing the ingestion of particulate debris larger than 1.0 μm. diameter. It is recognized, however, that smaller debris and debris with a condensable coating can deposit and accumulate over long time periods. It is desirable, therefore, to remove such deposits from the system periodically by cleaning with hot gases or liquids. The systems 10 and 110 as fabricated, are capable of prolonged exposure to maximum temperatures in excess of 100° C.

Figure 13:
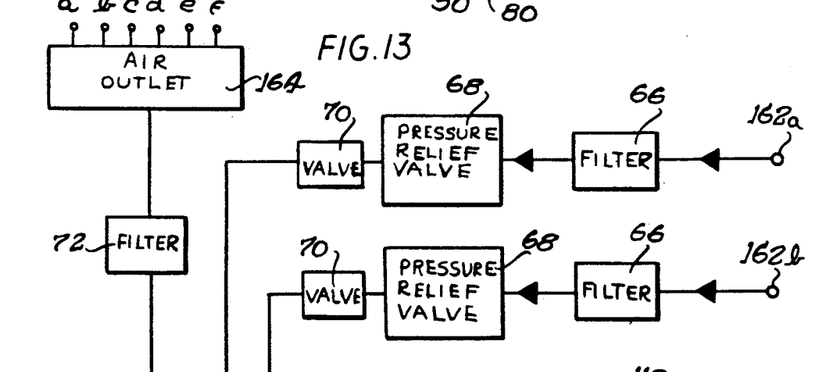
FIG. 13 is a schematic diagram illustrating a pneumatic circuit for use in the system of FIG. 11.

Overpressurization of the implants 12 and 112 with carrier gas can affect significantly their life and operation. For example, in the event the tubular membrane 44 is ruptured or the O-ring seals 56 are broken, the damage is total, i.e., the implant must be retrieved and repaired or abandoned. To minimize the probability of overpressurization, the interface pneumatic networks shown in FIGS. 9 and 13 are equipped with the pressure relief valves 68 and the downstream shutoff valves 70 in the carrier and calibration gas lines. It is a preferred startup procedure that after the carrier and calibration gas supply and control network 20 or 120 is connected to the interface module 18 or 118, operation begins with a functional and pressure setting check of the relief valves 68 with the shutoffs 70 in the closed position.

The systems 10 and 110 instabilities are a function of the parameters included in equations (1) and (4). Two of the more important parameters are external to the systems: (a) the carrier gas flow rate, $Q_c$, and (b) pressure, $P_c$. Instabilities in these, however, are associated directly with the carrier and calibration gas supply and control network. Standard pneumatic design techniques and components available commercially can be used to maintain $Q_c$ and $P_c$ within $\pm 1$ percent over $\pm 50°$ F. (10° C.) temperature range.

One of the most important parameters of the systems is the tubular membrane permeability coefficient, $P_m$, because it can be the most variable parameter under normal operating conditions and will determine directly the magnitude of the soil gas flow rate, $Q_s$, into the implant. $P_m$ varies exponentially with the tubular membrane absolute temperature. For example, near 20° C., the soil gas $P_m$ for Teflon materials varies approximately 1 percent/° C. Variations in soil temperature at the depth of the implant will be reflected in proportional variations of $Q_s$ and $[G]_s$. Thus, more stability in implant performance can be obtained by temperature-controlling the implant or by temperature compensation of $[G]_s$ with the output reading of a temperature probe that can be carried by the implant.

The system 10 is relatively stable as is evident from a review of its operating simplicity and design. Nevertheless, it may be preferable to utilize the distinct calibration provided in the system 110 independent of the appended analyzer/monitor to identify malfunctions and for troubleshooting purposes. A minimum calibration for an individual system includes:

a. Surface calibration with a standard innocuous gas,
b. Calibration with a variety of "typical" hazardous soil gas species, and
c. Periodic in situ calibrations with the standard innocuous gas.

This simple procedure identifies and quantifies drifts in the implant conductance, K, and malfunctions, such as leaking seals or membrane damage (tears or punctures). Because K is specific to each soil gas species, a complication arises that is addressed by invoking more sophisticated calibration procedures. After implantation of the implant, it is likely that site prospecting situations will develop in which K for specific soil gas species is undetermined. If the prospecting or monitoring data quality requirements can tolerate standard dimensional and material variations incurred in the manufacture of system 10, one needs only determine the implant 12 permeation conductance (K) for the specific soil gas species. This measurement can be performed by measuring the implant conductance for the soil gas species relative to a "typical" hazardous soil gas or the standard innocuous gas described earlier. If more precise and quantitative monitoring and analysis is required, however, each individual implant should be calibrated for each specific soil gas species. This can be accomplished only prior to implantation and therefore does not appear to be a practical alternative.

A more practical alternative appears to be invoking a calibration procedure that relates the conductance, K, of each system implanted to the conductance, $K_r$, of a reference system maintained in a laboratory. Thus, the conductance ratio, $K/K_r$, is determined for a standard gas for each system prior to its deployment. Thereafter, the conductance of a deployed system for any soil gas species, $K_{sg}$, may be determined from a measurement of the reference system conductance, $K_{rsg}$, for the same soil gas species:

$$K_{sg} = (K/K_r) K_{rsg} \qquad (8)$$

It is important to examine the magnitude and significance of the soil gas sample size or soil gas flow rate into the implant. The maximum typical soil gas sample flow rate into the implant is approximately 0.01 std. ml./min for arbitrary but realistic conditions. This estimate is based on a membrane material with $P_m = 2 \times 10^{-9}$ ml./min.−cm.$^2$−torr/cm. at 20° C. In a relative sense, it is a very small sample yet large enough to produce a [G] for many soil gas species within the response range of many gas phase analyzer/monitors that may be attached to the interface module 16 or 116.

There are two important aspects to the relatively small sample size or flow rate:

a. The disturbance to the soil is minimized; consequently, a more representative sample is obtained independent of soil fluid conditions.

b. For most soil strata in and around dump sites, the controlling soil gas flow rate impedance is 1/K of equations (2) and (5) and nearly independent of the gas viscosity and permeability of the surrounding soil. This condition also leads to a more representative soil gas sample in that the sample thus obtained is independent of soil conditions and soil gas viscosity.

An examination of equations (2), (3), and (4), shows that the soil gas flow rate is proportional to the soil gas species partial pressure without regard to the form of the sample, i.e., gas phase, liquid phase, or dissolved gas/liquid phase. For example, the implant can obtain information regarding dissolve trichloroethylene (TCE) in water or TCE separated from water, and insoluble gases contained in the water. Furthermore, the implants 12 and 112 can function adequately immersed completely in an aquifer or in a body of water or liquid. The small soil gas sample size and/or small soil gas flow rate and the utility of the implant in soil gases or liquids project some implications regarding site prospecting. For example, the form of the subsurface gases and their source may be inferred definitely from the concentration readings obtained on the surface and information as to the soil temperature at the sampling point. After identification of the soil fluid species and species vapor pressure data, the form of the subsurface fluid can be established. For example, if the partial pressure level measurement is equal to the fluid species liquid phase vapor pressure, it can be inferred that the fluid is present at the sampling point in the liquid phase. If the partial pressure is less than the vapor pressure, then it can be inferred that the fluid is present at the sampling point in the gas phase only or that it may be dissolved in a second fluid such as water.

Another important aspect of the implant operation is its efficiency in transporting highly polar molecules through the pneumatic lines to the interface. Polar molecules with relatively low vapor pressures, such as TNT, will be difficult to transport efficiently at low concentrations. The low vapor pressure promotes the condition whereby proportionally only low concentrations of the molecules are available in gas phase. The low concentrations compounded with the generally high adsorptivity of polar molecules on most surfaces promote inefficient transport through small diameter conduits and low gas flow rates. It is probable, at standard temperatures, that only a small fraction of highly polar molecules are transported through the entire length of the carrier gas return pneumatic lines. Therefore, it could become necessary to heat the transport lines or treat chemically the inside surface of the return lines to obtain efficient and repeatable transport of polar gas molecules from the implant to the interface.

The actual soil gas monitoring and analysis of the carrier or transport gas output stream from the interface module 58 or 158 is a simple and direct procedure. A variety of analyzers, monitors, and secondary sampling devices can be used singularly or simultaneously. Included among analyzers/detectors that may find use in this invention, depending on requirements, are thermal conductivity detectors, flame ionization detectors, photo-ionization detectors, electron-capture detectors, non-dispersive infrared analyzers, gas chromatograph type analyzers, mass spectrometer analyzers, and combination mass spectrometer/gas chromatograph analyzers. The user however must establish preliminary requirements for the target species and the lower detection limits of the analytical devices contemplated, i.e., it is essential to consider the analyzer/monitor performance specifications to specify and adjust the operating conditions of the system 10 or 110.

The basic function of the systems 10 and 110 is to lift soil gases to the surface in a form suitable for on-site analysis/monitoring and secondary sampling, i.e., at concentration levels above the analyzer/monitor lower detection limit in a non-interfering carrier gas. Thus, all system soil gas species required concentration levels are established directly by the analyzer/monitor performance specifications. The converse relationship can also apply. For example, the soil fluid species vapor pressure and its dispersed condition together with system performance will establish the concentration range of the gas species obtained at the interface and will define the most adequate analyzer/monitor.

Table 1 illustrates performance characteristics of the systems 10 and 110 for a variety of soil fluid species, including gases and liquids and a dissolved liquid in liquid water. Equations (1) through (7) were used to obtain the system performance estimates. In addition, the tubular membrane permeability coefficients for all the fluid species listed except water is assumed at $2 \times 10^{-9}$ std /ml./min.-cm$^2$-torr/cm. This assumption is a reasonably close approximation used only to obtain an estimate of the fluid species concentration at the surface. It is a reasonable assumption that the concentration levels obtained for each fluid species can range from $\frac{1}{3}$ to 3 times those listed in Table 1.

TABLE 1

ESTIMATED SAMPLING SYSTEM PERFORMANCE FOR SOIL GAS CONCENTRATION AT INTERFACE MODULE

Sampling Module Dimensions: Length - 6 in., Tubular Membrane Diameter - 6 in., Membrane Thickness - 0.001 in.
Soil Temperature: 20° C.
Tubular Membrane Material Permeability Coefficient: $2 \times 10^{-9}$ std ml/min-cm$^2$-torr/cm
Assumption: Permeability Coefficient Identical for All Soil Gas Species Except Water

| | SOIL GAS | | DYNAMIC SAMPLING $[G]_s^{++}$ | | STATIC SAMPLING | | |
|---|---|---|---|---|---|---|---|
| | | | | | $[G]_s^{\#}$ | | $T_V$ |
| Species | $P_{sg}$ (torr) | $Q_s^+$ (std ml/min) | $Q_c = 30$ std ml/min | $Q_c = 1$ std ml/min | Max. | Ave. | (days)$^{\#\#}$ |
| Hexane | 140 | $1.2 \times 10^{-2}$ | 400 ppm | 12,000 ppm | — | — | — |
| TCE | 60 | $5 \times 10^{-3}$ | 168 ppm | 5,040 ppm | — | — | — |
| TCE in H$_2$O* | 0.0082** | $6.9 \times 10^{-7}$ | 2.3 ppb | 69 ppb | 11 ppm | 2 ppm | 3.2 |
| TCE @ 1 ppm in H$_2$O* | $8.2 \times 10^{-6}$** | $6.9 \times 10^{-10}$ | 2.3 ppt | 69 ppt | 11 ppb | 2 ppb | 3.2 |
| TNT | $1.52 \times 10^{-6}$ | $1.3 \times 10^{-10}$ | 4.3 ppt | 129 ppt | 2 ppb | 400 ppt | ≧3.2 |
| Water*** | 17 | $1.42 \times 10^{-4}$ | 4.8 ppm | 144 ppm | — | — | — |
| PCB (C$_{12}$H$_7$Cl$_3$) | $9.0 \times 10^{-4}$ | $7.7 \times 10^{-8}$ | 2.6 ppb | 78 ppb | 1.2 ppm | 240 ppb | 3.2 |

*TCE Solubility in Water @ 20° C.: 0.1 g/100 g
**TCE Partial Pressure Estimate per Raoult's Law, W. J. Moore, Physical Chemistry, 4th ed., Prentice Hall, Inc., 1972, p. 237.
***Tubular Membrane Material Water Vapor Permeability Coefficient: $1.7 \times 10^{-10}$ std ml/min-cm$^2$-torr/cm
+ Equations (2) and (3)
++ Equation (1)
Equation (5)
Equation (7)

An examination of Table 1 provides revealing insight on the systems' 10 and 110 performance. For example, hexane and TCE exerting partial pressures near their respective vapor pressures will exhibit relatively high concentrations at the surface regardless of the carrier gas flow rate. Rapid analysis/monitoring can be accomplished in the dynamic sampling mode with instruments using relatively insensitive devices such as a flame ionization detector (FID) or a nondispersive infrared detector (NDIR). Using a dry carrier gas, the maximum carrier gas water vapor content at the surface will be in the low ppm range and thus pose only a negligible interference to the FID or NDIR response. It is probable that on-site analysis/monitoring of hydrocarbons exerting a minimum vapor or partial pressure of 0.5 torr can be performed by an FID or NDIR unit at a 30-std. ml./min. carrier gas flow rate. Correspondingly higher concentrations of these hydrocarbons can be obtained at lower carrier gas rates as shown by Table 1. The analysis/monitoring for TCE in liquid water saturated with TCE requires a more sensitive detector such as an electron capture detector. For a dynamic sampling situation at a carrier gas flow rate of 30 std ml./min., the resulting TEC concentration at the surface will be near 2.3 ppb.

For a dilute solution of TCE in liquid water, the surface concentration is in the low ppt range and the analytical requirements become more severe. This condition will need more extensive sample preparation such as that provided by special-purpose gas chromatographs, or other forms of preconcentration may be needed. For very low vapor pressure materials such as TNT and many polynuclear aromatic hydrocarbons, analytical equipment with identical performance specifications will be needed.

An alternative to performing the analytical/monitoring functions at low concentration levels near the analytical equipment lower detection limit is available in the static sampling mode. Table 1 shows the system 10 performance estimates in the static sampling mode for low vapor or partial pressure soil gas species such as TNT, a PCB, and dilute aqueous solutions of TCE. It should be noted that the maximum and average concentrations of these species in the static sampling mode range from approximately 1 to 2 orders of magnitude larger than the concentrations in the dynamic sampling mode. For example, after a 3.2-day waiting period, the system 10 or 110 will produce an 11-ppb gas sample for the TCE 1-ppm aqueous solution in the static sampling mode as opposed to a 2.3 or 69-ppt concentration in the dynamic sampling mode at carrier gas flow rates of 30 and 1 std. ml./min., respectively. An identical result is obtained with TNT and the PCB species.

The estimates obtained and listed in Table 1 present preliminary operational and design constraints to which the surface analytical equipment and the carrier and calibration gas supply control network should conform.

Figure 15:
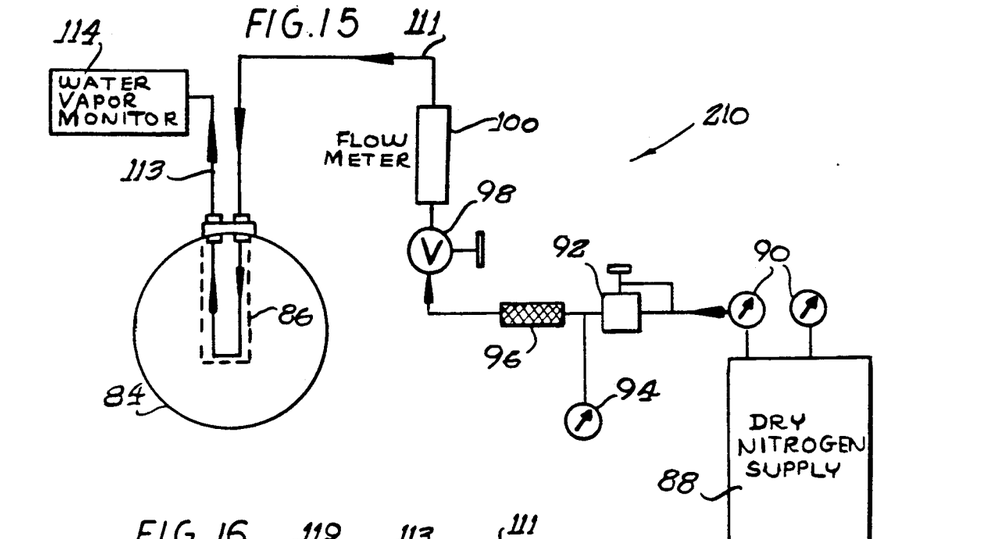
FIG. 15 is a schematic diagram illustrating the use of the invention in detecting contaminants in flue gases.

As alluded to earlier, a need also exists for a simple and reliable water vapor content monitor for hazardous waste incinerator flue streams. The foregoing principles are generally effective for this purpose with some variation in the structural elements and operation. In general, a flue gas system 210 is also provided that includes any suitable water vapor monitor available commercially and a water vapor mass exchange module. FIG. 15 illustrates schematically a deployment of such a system 210 in a flue 84 which may contain a hot gas stream. The embodiment of the system 210 depicted includes a water vapor mass exchanger 86 mounted through the wall of the flue 84 to extend inwardly toward the center of the flue cross section as shown to be in the flow of the hot flue gases. This exchanger 86 is described in more detail later. The system further includes a gas supply which includes a dry nitrogen reservoir 88 having a tank regulator 90 which is connected to a pressure regulator 92, a pressure gage 94, and a filter 96. The line continues to a flow adjust valve 98 and a flowmeter 100, all a part of the gas supply which is connected by way of an input line 111 to the mass exchanger 86. The output of the exchanger is connected by way of an exchanger output line 113 to a water vapor monitor 114. For most operations, the carrier gas supply, the pneumatic network components, and the water vapor monitor are items available commercially.

Operation of the depicted system 210 is as follows: (a) dry nitrogen gas or any suitable dry gas flows at a controlled and metered rate from the reservoir 88 through the pneumatic control elements 90–100 to the mass exchanger 86; (b) flue gases, and in particular water vapor, flow by a diffusion process into the mass exchanger 86, which is essentially a segment of semipermeable tubing such as Teflon; (c) the dry nitrogen carries gas and water vapor from the flue stream mix in the mass exchanger 86; and (d) the mixture is transported to the water vapor monitor 114 where the resulting water vapor content of the carrier gas is analyzed and measured.

Figure 16:
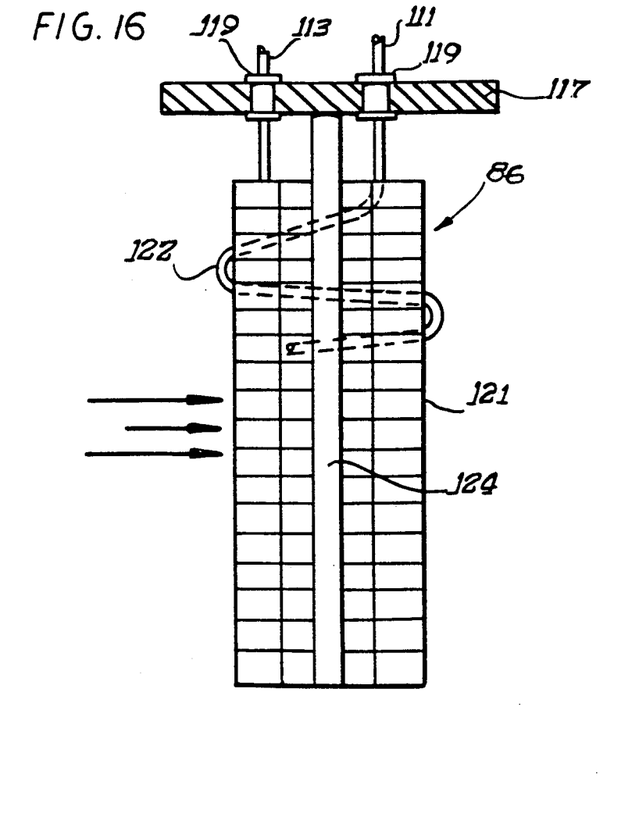
FIG. 16 is an enlarged view showing further details of the mass exchanger portion of the schematic of FIG. 15.

FIG. 16 illustrates the basic configuration of the mass exchanger 86 which is important in the operation of the invention. It includes a 3-inch (7.62 cm) diameter flange 117, two bulkhead fittings 119, a wire cage spool 121, and a 10-foot (3.05 m) segment of ⅛-inch (3.2 mm) O.D. Teflon tubing 122. The two bulkhead fittings 119 penetrate the flange 117 to permit the flow of nitrogen carrier gas through the tubing 122. The wire cage spool 121, which may be 2 inches (5.08 cm) in diameter and 5 inches (12.7 cm) long, is attached to the flange by a ¼ inch (6.4 mm) support rod 124, and the Teflon tubing 122 is wrapped loosely around the spool 121. For this application, the entire assembly is attached to the wall of the flue 84 such that the Teflon tubing 122 is exposed continuously to the flue gas stream.

In operation, carrier gas is flowing continuously from the dry nitrogen reservoir 88 through the Teflon tubing 122 and to the water vapor monitor 114. Simultaneously, water vapor carried by the flue gas flows through the Teflon tube wall by the diffusion process previously described and is mixed with the carrier gas. The water vapor flow rate is described by $$Q_w = 2\pi L\, P_m\, P_s / \ln(r_o/r_i)$$

where
$Q_w$ = water vapor flow rate into Teflon tube, std ml/min;
$L$ = Teflon tube length, cm;
$P_m$ = Teflon water vapor permeability coefficient, std ml/min-cm²-atm/cm;
$P_s$ = water vapor partial pressure at Teflon tube external surface, atm;
$r_o$ = Teflon tube outside radius, cm; and
$r_i$ = Teflon tube inside radius, cm.

The resulting concentration of the water vapor in the carrier gas at the water vapor monitor is $$[\text{Water Vapor}] = Q_w/Q_c$$

where
$Q_c$ = carrier gas flow rate, std ml/min.

$Q_w$ is dependent exponentially on the absolute temperature of the Teflon or the flue gas temperature.

Thus, a flue gas temperature reading is necessary to obtain a more precise measurement of flue gas water content for those applications where there are wide variations in flue gas temperature during normal operation. For this purpose, a thermocouple (not shown) can be attached near the end of the support rod 124 of the mass exchanger 86, or a thermocouple can penetrate the flange 117. The water vapor monitor 114 readout will be corrected by a factor related to flue gas temperature.

The water vapor concentration in the carrier gas will respond to a step change in flue gas water vapor concentration as follows:

$$T_R = 2.5\,(r_o^2 - r_i^2)\,\ln(r_o/r_i)\,/D_w$$

where
$T_R$ = carrier gas water vapor time rate-of-response to 90 percent, s, and
$D_w$ = Teflon water vapor diffusion coefficient, cm²/s.

Table 2 lists the flue gas system 210 performance estimates and the corresponding operating conditions and dimensions of the water vapor mass exchanger 86. For a 10 ml/min carrier gas flow rate and a 300° F. (148.74° C.) flue stream containing 11 percent (v/v) water vapor, the dew point of the sample will be 8° F. (−13.3° C.). This is within range of humidity instrumentation available commercially. Changes to the mass exchanger, however, can provide a different water vapor concentration in the carrier gas. For example, by reducing the carrier gas flow rate from 10 ml/min to 1 ml/min, the carrier gas dew point will increase from 8° F. (−13.3° C.) to 62° F. (16.65° C.). An examination of the equations above and Table 2 will show that other parametric changes are available for manipulation of the flue gas system dew point if desired.

TABLE 2
FLUE GAS SYSTEM PERFORMANCE ESTIMATES

Conditions at 300° F. (148.74° C.) for Teflon tubing
Length (L) - 10 feet (3.05 m)
Outside Diameter - ⅛ inch (3.2 mm)
Wall Thickness - 0.030 inch (.762 mm)
Permeability Coefficient ($P_m$) - $6 \times 10^{-5}$ std ml/min-cm$^2$-atm/cm for water
Water Vapor Partial Pressure - 0.11 atm
Diffusion Coefficient - $1 \times 10^{-3}$ cm$^2$/s
Performance
Water Vapor Diffusion Flow Rate ($Q_w$) - $1.93 \times 0^{-2}$ std ml/min
Carrier Flow Rate ($Q_c$) - 10 std ml/min
Water Vapor Content in Carrier Gas - 0.193 percent (v/v)
Carrier Gas Dew Point - 8° F. ($-13.3°$ C.)
Time Rate-of-Response - 30 seconds For practical purposes, the flue gas system 210 operates independently of the flue gas flow rate.

Response time is proportional (approximately) to the square of the tube wall thickness. Thus, use of Teflon tubing of 0.010 inch (0.254 mm) could reduce the rate-of-response from 30 seconds to 3.34 seconds. Further reduction could be accomplished with thinner-walled tubing such as might be needed in a more complicated system.

The properties of the Teflon tube as a diffusion medium may limit the temperature of the flue gas in which the system can operate. An in-line cooler (not shown) may be added to the system whereby the hote gases are extracted from the flue, passed through the cooler to cool the gas to Teflon temperature working levels and yet be above the flue gas water dew point. The gases then would pass the mass exchanger 86 and then the flue gas would be returned to the flue stack.

Summarizing, the soil gas sampler implant systems 10 and 110 are viable systems that provide representative samples of all soil gases and the flue gas system 210 is viable for the detection of contaminants in gases. Gas samples are obtained that are independent of the soil permeability characteristics and flue gas flow rates. The systems can be used as prospecting tools to obtain preliminary information as to the composition of soil fluids. A network of implanted samplers deployed throughout a site will supply information regarding soil fluid mobility or stability for the service life of the systems. The systems do not provide, however, a direct measurement of soil fluid loading as obtained by core samples. The systems also serve to detect contaminants in liquid masses and gases.

The foregoing description of the invention is given by way of a preferred embodiment and alternative embodiments. It should be recognized that deviations in form and details may be made by one skilled in the art without departing from the spirit and scope of this invention which is defined by the following claims.

What is claimed is:

1. In a sampler system for underground testing for contaminants, an implant having a gas permeable tube wall portion for collecting a gas sample from the soil in an underground zone, the flow of gas into the implant when inserted in the soil having a total impedance composed of a tubular membrane diffusion impedance of the gas permeable tube wall portion and a soil gas impedance in series therewith, the tube wall material and structure being such that the tubular membrane diffusion impedance is low enough to allow gas flow through the membrane while at the same time is high enough when compared to the soil gas impedance to effectively render the soil gas impedance insignificant, whereby the property of tubular membrane diffusion impedance of the tube wall portion substantially represents the total diffusion impedance to soil gas flowing from the soil into the implant.

2. An implant in accordance with claim 1 wherein the underground zone includes a stream of flowing water and the flow of gas into the implant emanates from the flowing stream.

3. In a sampler system for environmental testing for contaminants, a test module having a gas permeable tube wall portion for collecting a gas sample from a given zone of the environment when the test module is placed therein, the flow of gas into the test module having a total impedance against it composed of a membrane diffusion impedance of the gas permeable tube wall portion and an external gas impedance in series therewith, the tube wall material and structure being such that the tubular membrane diffusion impedance is low enough to allow gas flow through the membrane while at the same time is high enough when compared to the external gas impedance to effectively render the external gas impedance insignificant, whereby the property of tubular membrane diffusion impedance of the tube wall portion substantially represents the total diffusion impedance to gas flowing into the test module.

4. A test module in accordance with claim 3 wherein the module includes a supporting cage structure and the permeable tube wall portion is an extended length of Teflon tubing material wrapped in spiral form around the cage of disposition in a flue of flowing gas from an incinerator.

5. A test module in accordance with claim 4 wherein the Teflon tubing is approximately three meters long and has a wall thickness of approximately 0.76 mm.

6. A test module in accordance with claim 4 wherein the Teflon tubing is approximately three meters long and has a wall thickness of approximately 0.25 mm.

* * * * *

UNITED STATES PATENT AND TRADEMARK OFFICE
CERTIFICATE OF CORRECTION

PATENT NO.   : 5,010,776
DATED        : April 30, 1991
INVENTOR(S)  : Daniel P. LUCERO et al.

It is certified that error appears in the above-identified patent and that said Letters Patent is hereby corrected as shown below:

Title Page:

[56] References Cited, U.S. PATENT DOCUMENTS, line 13, change "4,821,565" to --4,821,585--, and change "Kampe" to --Kempe--.

[56] References Cited, OTHER PUBLICATIONS, in the "U.S. Army Corp." reference, line 3, change "pp. i-14 iii" to --pp. i-iii--.

[56] References Cited, OTHER PUBLICATIONS, in the "EPA Project Summary" reference, line 3, change "EPX/600/S2-86/001" to --EPA/600/S2-86/001--.

Column 10, line 5, after "membrane" insert a period.
Column 12, line 64, change "cm. $^2$/sec ," to --cm.$^2$/sec.,--.
Column 23, line 18, in TABLE 2, change "- 8°F." to --˜ 8°F.--.
Column 23, line 19, in TABLE 2, change "- 30 seconds" to --˜ 30 seconds--.
Column 23, line 33, change "hote" to --hot--.

Signed and Sealed this

Fifteenth Day of September, 1992

Attest:

DOUGLAS B. COMER

*Attesting Officer*   *Acting Commissioner of Patents and Trademarks*